United States Patent
Koizumi et al.

(10) Patent No.: US 10,052,411 B2
(45) Date of Patent: Aug. 21, 2018

(54) METHODS OF TREATING CORNEAL RELATED DISEASES BY CORNEAL ENDOTHELIAL PREPARATION WHICH ENABLES CELLS TO GROW IN VIVO

(75) Inventors: Noriko Koizumi, Kyoto (JP); Shigeru Kinoshita, Osaka (JP); Yuji Sakamoto, Kobe (JP)

(73) Assignee: SENJU PHARMACEUTICAL CO., LTD., Osaka-shi, Osaka (JP)

( * ) Notice: Subject to any disclaimer, the term of this patent is extended or adjusted under 35 U.S.C. 154(b) by 0 days.

(21) Appl. No.: 12/161,433

(22) PCT Filed: Jan. 18, 2007

(86) PCT No.: PCT/JP2007/050657
§ 371 (c)(1),
(2), (4) Date: Oct. 15, 2008

(87) PCT Pub. No.: WO2007/083685
PCT Pub. Date: Jul. 26, 2007

(65) Prior Publication Data
US 2010/0233240 A1 Sep. 16, 2010

(30) Foreign Application Priority Data
Jan. 19, 2006 (JP) .................................. 2006-011521

(51) Int. Cl.
| | | |
|---|---|---|
| A61K 48/00 | (2006.01) | |
| A01N 63/00 | (2006.01) | |
| C12N 5/07 | (2010.01) | |
| C12N 5/071 | (2010.01) | |
| C12N 5/16 | (2006.01) | |
| C12N 5/0793 | (2010.01) | |
| C12N 5/0789 | (2010.01) | |
| A61L 27/38 | (2006.01) | |
| A61L 27/24 | (2006.01) | |

(52) U.S. Cl.
CPC .......... *A61L 27/3839* (2013.01); *A61L 27/24* (2013.01); *A61L 27/3808* (2013.01); *A61L 2430/16* (2013.01)

(58) Field of Classification Search
CPC .. A61L 27/26; A61L 2430/16; A61L 27/3808; A61L 2300/236; A61L 27/222; A61L 27/24; A61L 27/3839; A61L 27/50; A61L 27/52; A61L 27/54; A61L 27/56; C08L 5/08; A61F 2/142; A61K 35/30
See application file for complete search history.

(56) References Cited

U.S. PATENT DOCUMENTS

| | | | |
|---|---|---|---|
| 5,374,515 A | 12/1994 | Parenteau et al. | |
| 6,679,898 B1 * | 1/2004 | Chuck | 606/166 |
| 7,959,939 B2 * | 6/2011 | Yamagami et al. | 424/423 |
| 2005/0214259 A1 | 9/2005 | Sano et al. | |
| 2007/0092550 A1 * | 4/2007 | Lui | 424/427 |
| 2007/0148137 A1 | 6/2007 | Okano et al. | |
| 2007/0238173 A1 | 10/2007 | Yamagami et al. | |
| 2008/0050423 A1 * | 2/2008 | Hsiue et al. | 424/443 |

FOREIGN PATENT DOCUMENTS

| | | |
|---|---|---|
| EP | 1 604 695 A1 | 12/2005 |
| JP | 2004-024852 A | 1/2004 |
| JP | 2005-229869 A | 9/2005 |
| WO | WO 2003/092762 A1 | 11/2003 |
| WO | WO 2004/073761 A1 | 9/2004 |
| WO | WO 2005/037144 A2 | 4/2005 |
| WO | WO 2005/078071 A1 | 8/2005 |

OTHER PUBLICATIONS

Manche et al. Arch Opthalmol. 1999; 117:1561-1565.*
Koizumi, *Japanese Journal of Clinical Ophthalmology*, 59 (11): 197-201 (2005).
Mimura et al., *Investigative Ophthalmology & Visual Science*, 45 (9): 2992-2997 (2004).
European Patent Office, Supplementary European Search Report in European Patent Application No. 07706961 (dated Apr. 11, 2012).
Matsubara et al., *Jpn. J. Ophthalmol.*, 26: 264-273 (1982).
Matsubara et al., *Jpn. J. Ophthalmol.*, 27: 444-450 (1983).
Tsuru et al., *Jpn. J. Ophthalmol.*, 28: 105-125 (1984).
Japanese Patent Office, International Search Report in International Patent Application PCT/JP2007/050657 (dated Feb. 13, 2007).
Fujita et al., *Ophthalmic Res.*, 49(3): 127-138 (2013).
Ishino et al., *Investigative Ophthalmology & Visual Science*, 45(3): 800-806 (2004 ).
Zhao et al., *J. Cataract Refract Surg.*, 34: 1715-1719 (2008).

* cited by examiner

*Primary Examiner* — Chang-Yu Wang
(74) *Attorney, Agent, or Firm* — Leydig, Voit & Mayer, Ltd.

(57) ABSTRACT

The present invention provides a graft more suitable for the transplantation of corneal endothelial cells and an application method thereof. Specifically, the present invention provides a corneal endothelial preparation capable of cell proliferation in vivo, which contains a substrate and a corneal endothelial cell layer cultured on the substrate, and a treatment method of a disease selected from the group consisting of bullous keratopathy, corneal edema, corneal leukoma and corneal endothelial inflammation, which includes a step of transplanting the preparation to patients. As the substrate, collagen is used.

45 Claims, 4 Drawing Sheets

6 months after transplantation

Normal

Formed basal membrane
Descemet's membrane

Descemet's membrane

Increased proliferation of corneal endothelial cells on the Descemet's membrane

Site where endothelial sheet was attached

AMEL

SRY

METHODS OF TREATING CORNEAL RELATED DISEASES BY CORNEAL ENDOTHELIAL PREPARATION WHICH ENABLES CELLS TO GROW IN VIVO

TECHNICAL FIELD

The present invention relates to a corneal endothelial preparation capable of cell proliferation in vivo, which is used as a graft for the treatment of corneal endothelial disorders.

BACKGROUND ART

Vision information is recognized when the light enters through the cornea, which is a transparent tissue at the front of the eye ball, reaches the retina to excite the retinal nerve cell that generates electric signals, which are transmitted to the cerebral visual area via the optic nerve. Good eyesight requires a transparent cornea. The transparency of the cornea is maintained since the pump function and barrier function of the corneal endothelial cell keep a constant water content.

The corneal endothelial cell density is about 3000 cells/$mm^2$ in human at birth. The cell has no ability to regenerate after damage. In endothelial corneal dystrophy and bullous keratopathy caused by functional disorder of corneal endothelium due to various etiologies, the corneal edema and opacity occur to markedly decrease vision. At present, penetrating keratoplasty for transplanting the whole three-layer structure of corneal epithelium, stroma and endothelium is performed for bullous keratopathy. However, corneal donation in Japan is insufficient, and the number of waiting patients for corneal transplantation is about 5500, but the number of corneal transplantation domestically performed per year is about 2700.

In an attempt to reduce the risk of rejection and postoperative complications, and acquire better visual function, the idea of "parts transplantation" for transplanting only the disordered tissue is attracting attention in recent years. Among the corneal transplantations, an epithelium transplantation procedure in which only the corneal epithelium is transplanted, an epithelium transplantation procedure of cultured oral mucous membrane in which mucous membrane is transplanted instead of the corneal epithelium, a procedure of deep layer and superficial layer corneal transplantation in which stromal tissue is transplanted, and the like have been performed. A method of transplanting only the corneal endothelium is under consideration. For transplantation of corneal endothelium, a corneal endothelium-like sheet comprising a corneal endothelial layer cultured on a collagen layer is known (see patent references 1 and 2). These sheets are expected to replace only the disordered endothelial cell layer with healthy endothelial cells by transplanting and supplementing corneal endothelium cultured in vitro, instead of penetrating keratoplasty performed heretofore for corneal endothelial diseases. However, since corneal endothelial cell is considered to have no ability to proliferate in vivo, a sufficient number of cultured cells are required to cover the area necessary for transplantation.
patent reference 1: JP-A-2004-24852
patent reference 2: JP-A-2005-229869

DISCLOSURE OF THE INVENTION

Problems to be Solved by the Invention

The present invention aims to provide a corneal endothelial preparation more suitable for the transplantation of corneal endothelial cells, namely, a graft for the treatment of corneal endothelium and an application method thereof.

Means of Solving the Problems

The present inventors have conducted intensive studies in view of the aforementioned problems and found that corneal endothelial cell conventionally considered impossible to proliferate in vivo can proliferate under certain conditions, which resulted in the completion of the present invention. Accordingly, the present invention provides the following.
[1] A corneal endothelial preparation capable of cell proliferation in vivo, which comprises a substrate and a cultured corneal endothelial cell layer.
[2] The preparation of the aforementioned [1], wherein the aforementioned substrate is collagen.
[3] The preparation of the aforementioned [1] or [2], which is in the form of a sheet.
[4] The preparation of any one of the aforementioned [1] to [3], which covers an area smaller than the area of a disordered corneal endothelium.
[5] The preparation of the aforementioned [4], which covers 10-90% of the area of the disordered corneal endothelium.
[6] The preparation of any one of the aforementioned [1] to [5], which remains attached to the Descemet's membrane or corneal stroma at least for 3 days after transplantation, and thereafter
(1) detaches itself or
(2) loses the substrate.
[7] The preparation of any one of the aforementioned [1] to [6], which is used for the treatment of a disease selected from the group consisting of bullous keratopathy, corneal edema, corneal leukoma and corneal endothelial inflammation.
[8] A method of treating a disease selected from the group consisting of bullous keratopathy, corneal edema, corneal leukoma and corneal endothelial inflammation, which comprises transplanting the corneal endothelial preparation of any one of the aforementioned [1] to [6] to a subject in need thereof.
[9] A method of proliferating a corneal endothelial cell, which comprises a step of transplanting a corneal endothelial preparation comprising a substrate and a cultured corneal endothelial cell layer to a patient to cover an area smaller than the area of a disordered corneal endothelium.
[10] A method of proliferating a corneal endothelial cell, which comprises a step of transplanting a corneal endothelial preparation comprising a substrate and a cultured corneal endothelial cell layer to a patient, wherein said preparation remains attached to the Descemet's membrane or corneal stroma at least for 3 days after transplantation, and thereafter
(1) detaches itself or
(2) loses the substrate.
[11] Use of a substrate and a cultured corneal endothelial cell layer on said substrate for the production of a corneal endothelial preparation capable of cell proliferation in vivo.
[12] The use of the aforementioned [11], wherein the aforementioned substrate is collagen.
[13] The use of the aforementioned [11] or [12], wherein the aforementioned preparation is in the form of a sheet.
[14] The use of any one of the aforementioned [11] to [13], wherein the aforementioned preparation covers an area smaller than the area of a disordered corneal endothelium.
[15] The use of the aforementioned [14], wherein the aforementioned preparation covers 10-90% of the area of the disordered corneal endothelium.

[16] The use of any one of the aforementioned [11] to [15], wherein the aforementioned preparation remains attached to the Descemet's membrane or corneal stroma at least for 3 days after transplantation, and thereafter
(1) detaches itself or
(2) loses the substrate.
[17] The use of any one of the aforementioned [11] to [16], wherein the aforementioned preparation is used for the treatment of a disease selected from the group consisting of bullous keratopathy, corneal edema, corneal leukoma and corneal endothelial inflammation.
[18] A commercial package comprising the corneal endothelial preparation of any one of the aforementioned [1] to [7] and a written matter relating to the preparation which states that the preparation can or should be used for the treatment of a disease selected from the group consisting of bullous keratopathy, corneal edema, corneal leukoma and corneal endothelial inflammation.

Effect of the Invention

According to the present invention, since a corneal endothelial preparation capable of cell proliferation in vivo is provided, it enables superior transplantation of a corneal endothelial graft, as well as growth of transplanted cells, thus affording a corneal endothelium regenerative effect, with a graft having a smaller area than conventional ones, i.e., a corneal endothelial preparation. The corneal endothelial preparation of the present invention can be utilized as a transplantation material to be used for the treatment of a disease requiring corneal endothelial transplantation, for example, bullous keratopathy, corneal edema, corneal leukoma, corneal endothelial inflammation and the like. Moreover, since the preparation of the present invention is superior in the cell proliferation, the substrate can be removed early after transplantation, which improves the postoperative QOV (Quality of Vision), and the visual acuity can be recovered early.

BEST MODE FOR CARRYING OUT THE INVENTION

Figure 1:
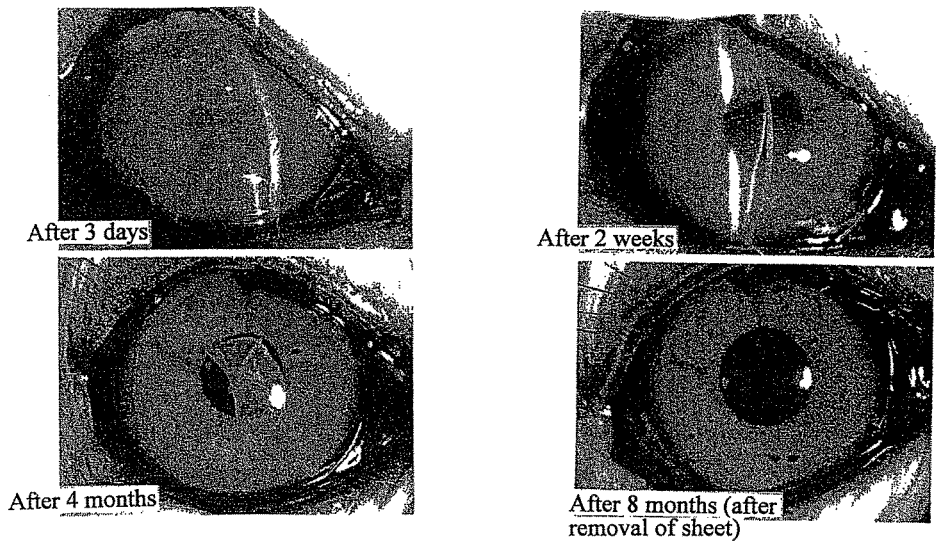
FIG. 1 shows photographs of the anterior ocular segment after transplantation of cultured corneal endothelial cells.
Figure 2:
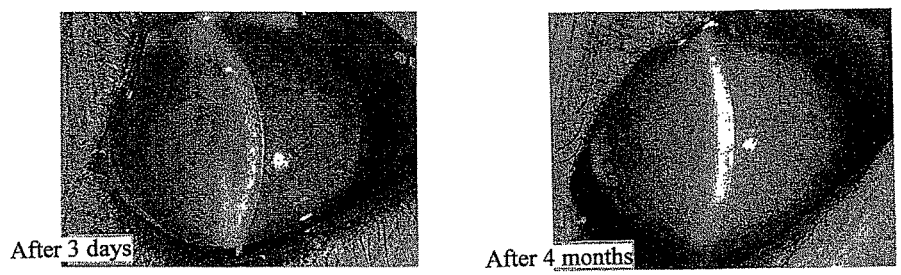
FIG. 2 shows photographs of the anterior ocular segment of the control eye.

The present invention provides a corneal endothelial preparation capable of cell proliferation in vivo. The preparation of the present invention is characterized by a laminate wherein a substrate and a cultured corneal endothelial cell layer are directly or indirectly laminated.

In the present invention, "capable of cell proliferation in vivo" means an ability of corneal endothelial cells to grow on the corneal stroma or Descemet's membrane in living organisms. Such ability can be confirmed through observation of postoperative progress with a corneal endothelial specular microscope.

In the present invention, the substrate is not particularly limited as long as it can carry a cultured corneal endothelial cell layer and maintain the shape thereof in vivo at least for 3 days after transplantation. In addition, the substrate may act as a scaffold for cultivating the corneal endothelial cells, or may only carry the corneal endothelial cell layer after culture. Preferably, the substrate is used for culturing the corneal endothelial cells and also acts as a scaffold that can be transplanted after completion of the culture.

Examples of the aforementioned substrate include polymer materials derived from naturally-occurring substances such as collagen, gelatin, cellulose and the like, synthesized polymer materials such as polystyrene, polyester, polycarbonate, poly(N-isopropylacrylamide) and the like, biodegradable polymer materials such as polylactic acid, polyglycolic acid and the like, hydroxyapatite, amniotic membrane and the like.

While the shape of the aforementioned substrate is not particularly limited as long as it can carry a corneal endothelial cell layer and is suitable for transplantation, a sheet form is preferable. When the preparation of the present invention is a sheet, it can be used after cutting into a size suitable for the application site during the transplantation. In addition, the sheet may be rolled small and inserted from a cut. A preferable specific example thereof is a disc shape covering about 30% of the area of a disordered corneal endothelium. It is also preferable to make a cut in a part surrounding the aforementioned disc shape, preferably toward the center, to allow close adhesion to the application site.

In a preferable embodiment, the aforementioned substrate is collagen. As the collagen, the collagen sheet described in JP-A-2004-24852 can be used preferably. Such collagen sheet can be prepared according to the method described in the aforementioned JP-A-2004-24852 from, for example, amniotic membrane.

The preparation of the present invention is a corneal endothelial preparation capable of cell proliferation in vivo, which comprises a substrate and a cultured corneal endothelial cell layer, wherein the cultured corneal endothelial cells are those cultured in vitro. Specifically, as the cultured corneal endothelial cells, (1) those cultured at least in a culture vessel (e.g., culture dish, culture tube, culture tank etc.), (2) such cells passage-cultured further (preferably, 3-10 passages), or (3) such passage-cultured cells that are further cultured on a substrate, are used.

The cultured corneal endothelial cell layer contained in the preparation of the present invention has at least one of the following characteristics. It preferably has two or more, more preferably all of the following characteristics.
(1) The cell layer has a monolayer structure. This is one of the characteristics of the corneal endothelial cell layer of living organisms.

(2) The cell density of the cell layer is about 1,000-about 4,000 cells/mm$^2$. Particularly, when the recipient (transplantee) is an adult, the density is preferably about 2,000-about 3,000 cells/mm$^2$.

(3) The visual flat plane shape of the cell constituting the cell layer is approximately hexagonal. This is one of the characteristics of the cell constituting the corneal endothelial cell layer in living organisms. The preparation of the present invention is similar to the corneal endothelial cell layer of living organisms, and exhibits a function similar to that of the inherent corneal endothelial cell layer, as well as an ability to proliferate in living organisms.

(4) In the cell layer, cells are regularly aligned. In the corneal endothelial cell layer in living organisms, the cells constituting the layer are regularly aligned, by which it is considered that the corneal endothelial cells maintain normal function and high transparency and the cornea appropriately controls the water content. Having such morphological characteristics, the preparation of the present invention is expected to show functions similar to those of the corneal endothelial cell layer in living organisms.

The preparation of the present invention can be produced, for example, by the following method.

<1> Collection of Corneal Endothelial Cells and Culture Thereof in a Culture Vessel (in a Test Tube: In Vitro)

Corneal endothelial cells are collected by a conventional method from the cornea of the recipient him/herself or a suitable donor. Homogeneous corneal endothelial cells are preferably prepared. For example, the Descemet's membrane and the endothelial cell layer of a corneal tissue are detached from the corneal stroma, transferred into a culture vessel such as a culture dish and the like, and treated with DISPASE and the like. As a result, the corneal endothelial cells are detached from the Descemet's membrane. The corneal endothelial cells remaining in the Descemet's membrane can be detached by pipetting and the like. After removal of the Descemet's membrane, the corneal endothelial cells are cultivated in a suitable culture medium permitting growth of corneal endothelial cells. As the culture medium, for example, commercially available DMEM (Dulbecco's Modified Eagle's Medium) appropriately supplemented with FBS (fetal bovine serum), b-FGF (basic-fiblo-blast growth factor) and antibiotics such as penicillin, streptomycin and the like can be used. The culture vessel (culture dish) used here preferably has a surface coated with Type I collagen, Type IV collagen, fibronectin, laminin or an extracellular matrix of bovine corneal endothelial cells and the like. Alternatively, a conventional culture vessel treated with a commercially available coating agent such as an FNC coating mix (registered trade mark) and the like may be used. In this way, adhesion of the corneal endothelial cell to the surface of a culture vessel is promoted and superior cell proliferation occurs.

The temperature condition for cultivating corneal endothelial cells is not particularly limited as long as they grow and is, for example, about 25-about 45° C., preferably about 30-about 40° C. and, in consideration of proliferation efficiency, more preferably about 37° C. As a cultivation method, the cells are cultured in a conventional incubator for cell culture under humidification in an environment of about 5-10% $CO_2$.

<2> Subculture

The cultured corneal endothelial cells after growth can be subjected to a subculture. Preferably, subconfluent or confluent cells are subjected to the subculture. The subculture includes the following steps. First, the cells are detached from the surface of the culture vessel by a treatment with trypsin-EDTA etc. and recovered. A culture medium is added to the recovered cells to give a cell suspension. A centrifugal treatment is preferably applied during or after recovery of the cells. Such centrifugal treatment affords a cell suspension with a high cell density. The conditions of the centrifugal treatment are, for example, 500 rpm (30 G)-1000 rpm (70 G), 1 to 10 minutes.

The cell suspension is seeded and cultured in a culture vessel in the same manner as in the above-mentioned primary culture. While the dilution ratio during passage varies depending on the condition of the cells, it is about 1:2-1:4, preferably about 1:3. Subculture can be performed under the same culture conditions as for the above-mentioned primary culture. While the culture time varies depending on the condition and the like of the cells to be used, it is, for example, 7-30 days. This subculture can be performed plural times where necessary.

<3> Preparation of Corneal Endothelial Cell Layer

The cell suspension is seeded and cultured on a substrate such as a collagen sheet and the like. At this time, the number of cells to be seeded is adjusted to form a cell layer having a desired cell density in the finally-produced corneal endothelial preparation. Specifically, the cells are seeded to form a cell layer having a cell density of about 1,000-about 4,000 cells/mm$^2$. The cultivation can be performed under the same conditions as in the above-mentioned primary culture and the like. While the culture time varies depending on the condition of the cells to be used, it is, for example, 3-30 days.

Cultivation in the above-mentioned manner affords a corneal endothelial preparation wherein a corneal endothelial cell layer cultured in vitro is formed on a substrate.

The preparation of the present invention may contain a carrier to maintain good viability of the corneal endothelial cells before transplantation. Examples of the carrier include a corneoscleral graft presentation solution OPTISOL-GS™, an eye ball preservation solution for corneal transplantation EPII™, saline, phosphate buffered saline (PBS) and the like.

The preparation of the present invention can be used as a graft for the treatment of a disease requiring a corneal endothelial transplantation, for example, bullous keratopathy, corneal edema, corneal leukoma and corneal endothelial inflammation, particularly, corneal dystrophy, bullous keratopathy caused by corneal endothelial disorder induced by trauma or intraocular surgery.

One example of the transplantation method is deep layer cornea excision. Firstly, a part of the corneal stroma of the recipient is detached, and a part of the corneal stroma deep layer and a part of the Descemet's membrane and endothelial cell layer are removed. Only the endothelial cell layer, or only the endothelial cell layer and Descemet's membrane may be removed. Then, the preparation of the present invention is inserted into the removed part(s) with a spatula and the like. To immobilize the graft, an adhesive such as a fibrin glue, fibronectin and the like may be used on demand. Where necessary, the air may be injected into the anterior chamber to immobilize the graft.

The preparation of the present invention preferably remains attached to the Descemet's membrane or corneal stroma at least for 3 days post-transplantation, and may be detached after day 3. For early detachment of the substrate, for example, the amount of the adhesive such as a fibrin glue, fibronectin and the like can be controlled. Moreover, a biodegradable material may be used for the substrate in the preparation of the present invention, so that the substrate will disappear after contact with the Descemet's membrane or corneal stroma for a predetermined period (e.g., at least 3 days). In this way, an improved postoperative QOV and earlier recovery of the visual acuity are expected. With the preparation of the present invention, viable adhesion of the corneal endothelial layer occurs in living organisms even when the substrate is detached, and the viably adhered cells can grow in the body. Therefore, the substrate does not need to be maintained at a transplantation site for a long time. The substrate that fell off in the anterior chamber can be removed within a given period after confirmation of the detachment. Even after early removal of the substrate, the cornea maintains transparency, and the recipient is basically expected to lead a normal life by around 2 weeks post-transplantation.

In addition, since the preparation of the present invention permits in vivo proliferation of the viably adhered cells, it may cover about 10-90%, preferably about 10-50%, more preferably about 20-40%, of the area of the disordered corneal endothelium. Since a small preparation can minimize the size of a cut, postoperative inflammation is mild and the possibility of postoperative infection can be decreased simultaneously.

Whether or not the transplanted corneal endothelial cell layer has a barrier function and a pump function as does the corneal endothelial cell layer in living organisms can be confirmed by, for example, examining the changes of corneal thickness and the development of edema after transplantation.

Accordingly, the present invention also provides a method of proliferating a corneal endothelial cell, which comprises a step of transplanting the preparation of the present invention to a patient to cover an area smaller than a disordered corneal endothelium. Moreover, the present invention provides a method of proliferating a corneal endothelial cell, which comprises a step of transplanting the preparation of the present invention to a patient, wherein said preparation remains attached to the Descemet's membrane or corneal stroma at least for 3 days after transplantation, and thereafter
(1) detaches itself or
(2) loses the substrate.

EXAMPLES

The present invention is explained in more detail in the following by referring to Examples, which are not to be construed as limitative. The animal experiments were performed according to the plan approved by Shiga University of Medical Science Animal Experiment Committee. The experimental animal was used according to the International Guiding Principles for Biomedical Research Involving Animals, as well as law relating to protection and management of animals, and standard relating to feeding and housing and the like of experimental animals. This experiment was performed according to Guidelines of the Association for Research in Vision and Opthalmology on the Use of Animals in Ophthalmic and Vision Research.

Example 1

Preparation of Cultured Corneal Endothelial Cell for Transplantation

A cynomolgus monkey (3 to 8 years old, male, Keari Co., Ltd.) was euthanized and the eye ball was removed. Corneal endothelial cells were collected together with the Descemet's membrane from the corneal tissue of the removed eye, and treated with DISPASE™ protease to separate the corneal endothelial cells. The separated corneal endothelial cells were seeded ($1\times10^5$ cells/well) on a 12 well culture plate (manufactured by Corning) coated with FNC COATING MIX™, and cultured in a culture medium (DMEM, manufactured by GIBCO Invitrogen) supplemented with 1% fetal calf serum and 2 mg/ml bFGF (Gibco Invitrogen) under the conditions of 37° C., 5% $CO_2$. When the cells reached confluent, they were detached by a Trypsin-EDTA treatment, and subcultured 3 times at a density of about 1:3. The cultured corneal endothelial cells were finally seeded on a collagen sheet (manufactured by AGC Techno Glass) at a density of 1:3, and cultured for 3-4 weeks under the same conditions as above to give a corneal endothelial sheet. The obtained corneal endothelial sheet was used for a transplantation test.

Example 2

Transplantation Procedure of Cultured Corneal Endothelium

Four cynomolgus monkeys (3-5 years old, female, KEARI Co., Ltd., CLEA Japan, Inc., LaboProducts Limited) were carried from the cage to a treatment table under systemic anesthesia by intramuscular injection of a mixed anesthesia of ketamine hydrochloride and xylazine hydrochloride. Inhalation anesthesia using a mask was started on the treatment table. After confirmation of the systemic stable conditions, about 5-6 mm of corneoscleral incision was performed in the sclera at 1 mm outside the limb, which is the boundary between cornea and conjunctiva, of 4 eyes (either eye) of the four monkeys, and the corneal endothelial cells were removed from the part as much as possible by physical scraping (diameter about 9 mm). The removed area of corneal endothelial cells was confirmed by Trypan Blue staining. The corneal endothelial sheet obtained in Example 1 was transplanted to the three eyes. As a control, a collagen sheet free of the cultured corneal endothelial cell was transplanted to one eye. The sheet was transplanted as shown below. That is, the anterior chamber was washed with an intraocular perfusion fluid (BBS-PLUS™), sodium hyaluronate (OPEGAN™) was injected thereinto to maintain the space in the anterior chamber, after which the 5 mm diameter corneal endothelial sheet (cell density: 2700 cells/$mm^2$) obtained in the above-mentioned Example 1 and coated with a slight amount of a fibrin glue on its entire sheet surface, or a collagen sheet (sheet alone) was inserted into the anterior chamber using a spatula. The corneal endothelial sheet was inserted such that the endothelial cell layer would be on the anterior chamber side. Then, the air sterilized by filtration was injected into the anterior chamber to allow adhesion of the sheet to the corneal stroma. Thereafter, the treated monkeys were maintained with the face up for about 20-30 min. The sclerocorneal wound was sutured with a 10-0 nylon yarn and the absence of leakage of the anterior chamber fluid from the eye was confirmed to complete the transplantation.

The monkeys were observed for 6 months post-transplantation, including observation and photographing of the anterior ocular segment with a slit lamp microscope, measurement of corneal thickness, and observation with a non-contact type corneal endothelial specular microscope (Konan Medica, NONCON ROBO SP-9000LC).

<Results>

Figure 3:
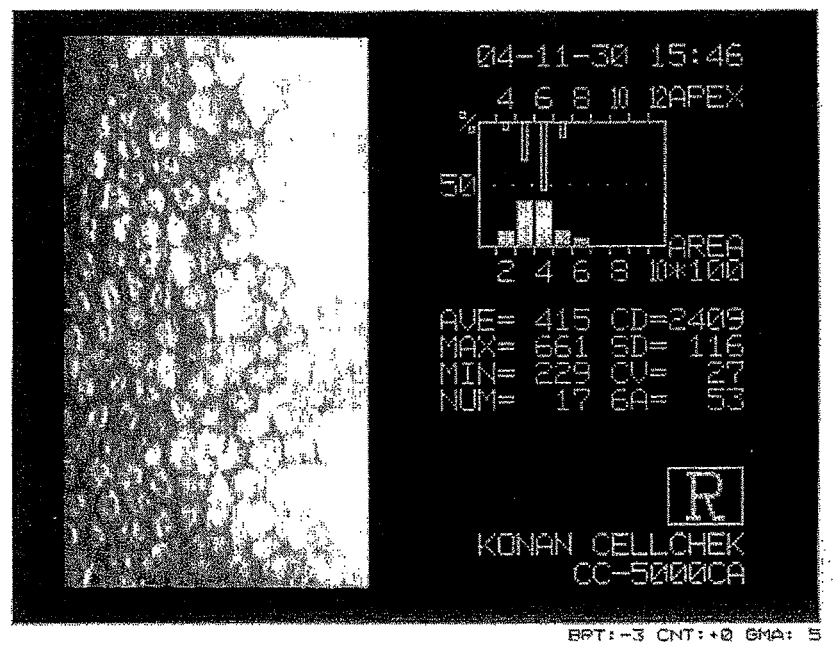
FIG. 3 is a specular micrograph of corneal endothelium at 6 months after transplantation of cultured corneal endothelial cells.
Figure 4:
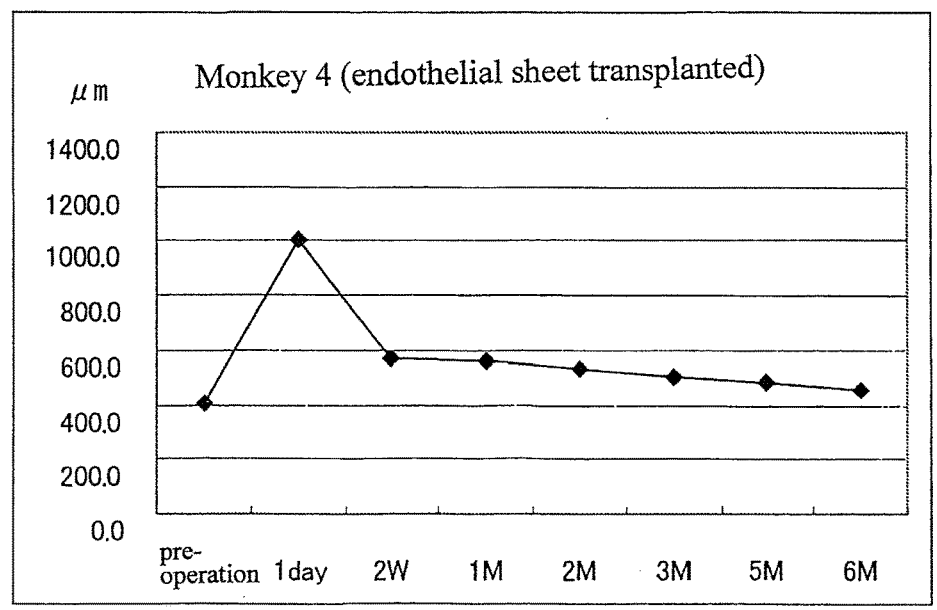
FIG. 4 is a graph showing changes in the corneal thickness of the eye before and after transplantation of cultured corneal endothelium.

In the corneal endothelial cell transplanted eye, the corneal endothelial sheet remained attached to the Descemet's membrane on the next day and 3 days after the transplantation, and the corneal edema was mild. Two weeks later, although the corneal endothelial sheet fell off in the anterior chamber, the cornea became transparent and maintained the transparency for 6 months (FIG. 1). As for the corneal thickness, corneal edema of about 1000 μm was confirmed immediately after transplantation. However, the edema gradually disappeared and the corneal thickness decreased to the thickness before the transplantation in about 3 months (FIG. 4). By observation with a non-contact type corneal endothelial specular microscope at 6 months later, hexagonal cells (about 2400/mm$^2$) were observed in the posterior surface of the cornea (FIG. 3). The corneal endothelial sheet that fell off after operation was removed at the time point of 6 months. The transparency of the cornea was maintained even thereafter, and a decrease in the endothelial cell density was not observed. Furthermore, an immunological rejection was not found up to the final observation. In contrast, the eye transplanted only with a collagen sheet without a corneal endothelial cell as the control suffered from severe corneal edema since immediately after the transplantation, which was not improved during the progress, and the corneal thickness and endothelial cell density were unmeasurable by a specular microscopy (FIG. 4).

Example 3

Histological Evaluation of Corneal Endothelium

Figure 5:
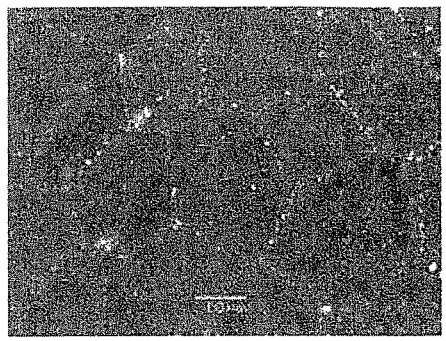
FIG. 5 shows electron micrographs at 6 months after transplantation of cultured corneal endothelium (the right is the untreated eye).
Figure 5:
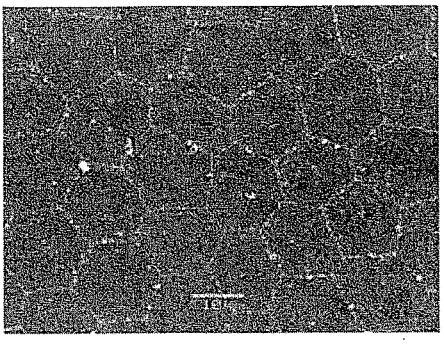
Figure 5:
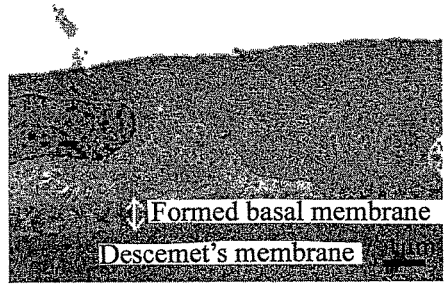
Figure 5:
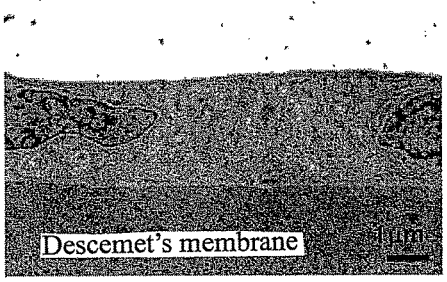

Among the 4 cynomolgus monkeys that underwent the cultured corneal endothelial transplantation procedure in Example 2, two were euthanized at 6 months post-transplantation, and the isolated corneal tissue was observed with a scanning electron microscope and a transmission electron microscope.
<Results>
The both monkeys showed good adhesion between cells since polygonal corneal endothelial cells with a diameter of about 15-30 μm were arranged in one layer inside the cornea (where intrinsic corneal endothelial cells are to be present). In addition, a new basal membrane layer was formed between the corneal endothelial cell and the Descemet's membrane, an intrinsic basal membrane (FIG. 5). It is clear therefrom that the corneal endothelial cell adheres well to the back of the cornea, and constructs a cell biological structure similar to that of intrinsic corneal endothelial cells, thereby exhibiting the normal corneal endothelial function.

Example 4

Evaluation at 19 Months Post-Transplantation

Figure 6:
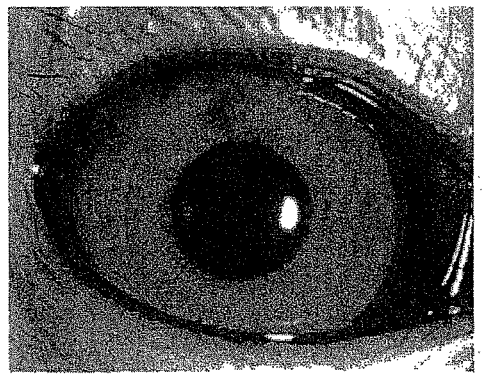
FIG. 6 shows a photograph of the anterior ocular segment and a specular micrograph of the corneal endothelium, both at 19 months after transplantation of cultured corneal endothelium.
Figure 6:
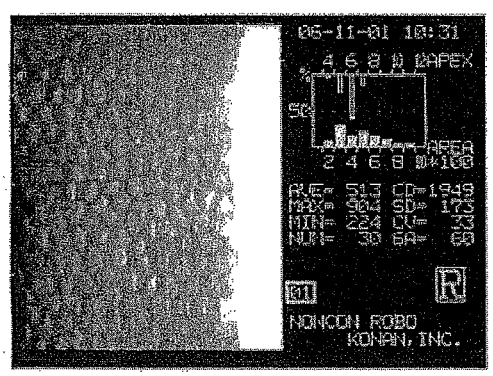

Among the 4 cynomolgus monkeys that underwent the cultured corneal endothelial transplantation procedure in Example 2, one was subjected to a long-term observation of corneal wound healing. The transparency of the cornea was maintained for 19 months post-transplantation, and about 1900 cells/mm$^2$ of corneal endothelial cells were maintained according to an observation with a non-contact type corneal endothelial specular microscope. Moreover, from the image analysis data of a specular microscope, the parameters of corneal endothelial cell were within the normal range as evidenced by a coefficient of variation (CV value) of 0.33 and hexagonal cell rate of 60, whereby the stable state of the corneal endothelial cell with less variation was clarified (FIG. 6).
<Conclusion>
As a result of the transplantation of cultured corneal endothelial cells to cynomolgus monkeys having a low capacity of corneal endothelial cell proliferation in vivo and the long-term observation for 6 months, the corneal endothelial cells at a density of about 2400/mm$^2$ were observed. The results suggest that the transplanted cultured corneal endothelial cells started to proliferate again in vivo. It was clarified that the corneal endothelial cells of a cynomolgus monkey considered to have, like human, an extremely low capacity of cell proliferation in vivo acquire the proliferative capacity again when they are once taken out from a living body and cultivated in an appropriate environment, and that the growth ability is maintained even after transplantation.

In addition, from the results of the long-term evaluation for 19 months in Example 4, it was shown that the preparation of the present invention can maintain the function of the corneal endothelium stably and well for a long time.

Example 5

Analysis of Corneal Endothelial Cell

Figure 7:
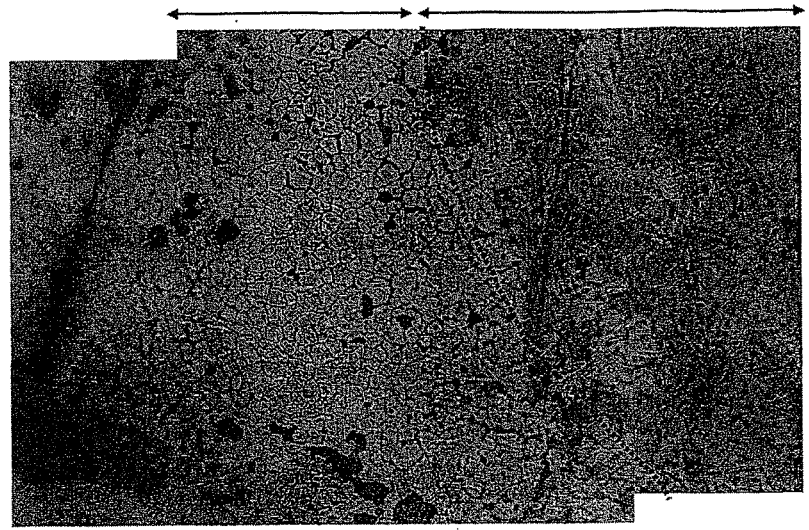
FIG. 7 shows a corneal tissue of a monkey at 1 week after transplantation of an endothelial sheet. The endothelial cells is proliferated and migrated around the site of the detached sheet.
Figure 8:
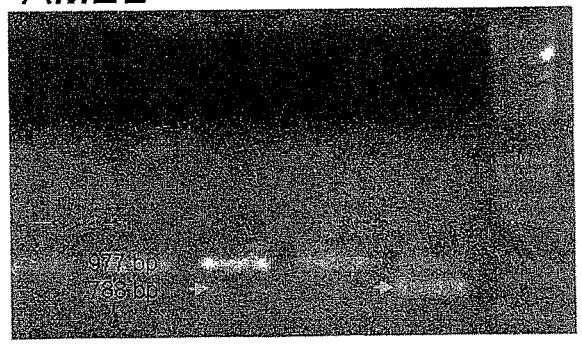
FIG. 8 shows analysis of a corneal tissue of a monkey by PCR for a male-derived gene at 1 week after transplantation of an endothelial sheet (lane 1: endothelial sheet transplanted eye; lane 2: control female; lane 3: control male; M1, M2: markers).
Figure 8:
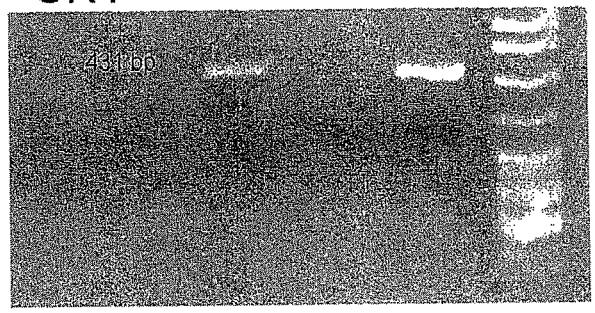

Using a corneal endothelial sheet prepared in the same manner as in Example 1, a cynomolgus monkey (4 years old, female, KEARI Co., Ltd.) was subjected to a corneal endothelial transplantation procedure in the same manner as in Example 2. At 1 week post-transplantation, the endothelial sheet fell off. The cornea at this time point was isolated, stained with alizarin, and only the endothelial cells were harvested by an impression cytology method. The collected sample was analyzed by PCR for ameleogenin gene (AMEL) and SRY gene, which are specifically expressed in Y chromosome found only in the male-derived cells. As a result, increased proliferation of corneal endothelial cells on the Descemet's membrane in the vicinity of the site where the endothelial sheet had been attached was confirmed by alizarin staining (FIG. 7). In addition, male-derived ameleogenin and SRY gene were detected in the corneal endothelial tissue after sheet detachment, suggesting that the cells grown on the Descemet's membrane were corneal endothelial cells derived from male (i.e., endothelial sheet) (FIG. 8).

The invention claimed is:
1. A method of treating a disease selected from the group consisting of bullous keratopathy, corneal edema, corneal leukoma and corneal endothelial inflammation, which comprises transplanting a corneal endothelial preparation capable of cell proliferation in vivo, to an eye of a human subject in need thereof,
   wherein the preparation comprises (a) a substrate selected from the group consisting of collagen, gelatin, cellulose, polystyrene, polyester, polycarbonate, poly(N-isopropylacrylamide), polylactic acid, polyglycolic acid, hydroxyapatite, and amniotic membrane, and (b) a cultured corneal endothelial cell layer, wherein the preparation covers 10-50% of the area of a disordered corneal endothelium of the subject, and
   wherein the transplanted corneal endothelial cells grow on the corneal stroma or Descemet's membrane in the vicinity of the site where the preparation is attached and further proliferate, thereby treating the disease.
2. The method of claim 1, wherein the substrate is collagen.
3. The method of claim 1, wherein the preparation is in the form of a sheet.
4. The method of claim 1, wherein the preparation is attached to the Descemet's membrane or corneal stroma of the subject for at least 3 days after transplanting the corneal endothelial preparation, and thereafter
   (1) detaches itself or
   (2) loses the substrate.
5. The method of claim 1, wherein the transplanting comprises performing a corneoscleral incision.
6. The method of claim 5, wherein the transplanting further comprises removing corneal endothelial cells from the eye of the subject following the corneoscleral incision.

7. The method of claim 6, wherein the transplanting further comprises washing the anterior chamber of the eye of the subject with an intraocular perfusion fluid.

8. The method of claim 7, wherein the transplanting further comprises injecting sodium hyaluronate to maintain the space in the anterior chamber.

9. The method of claim 8, wherein the corneal endothelial preparation is inserted into the anterior chamber.

10. The method of claim 9, wherein the transplanting further comprises injecting air into the anterior chamber.

11. The method of claim 10, wherein the transplanting further comprises maintaining the subject face up.

12. The method of claim 11, wherein the transplanting further comprises suturing the sclerocorneal wound.

13. A method of proliferating a corneal endothelial cell, which comprises a step of transplanting a corneal endothelial preparation capable of cell proliferation in vivo to an eye of a human patient with a disordered corneal epithelium,
wherein the preparation comprises (a) a substrate selected from the group consisting of collagen, gelatin, cellulose, polystyrene, polyester, polycarbonate, poly(N-isopropylacrylamide), polylactic acid, polyglycolic acid, hydroxyapatite, and amniotic membrane, and (b) a cultured corneal endothelial cell layer, wherein the preparation covers 10-50% of the area of the disordered corneal endothelium, and
wherein the transplanted corneal endothelial cells grow on the corneal stroma or Descemet's membrane in the vicinity of the site where the preparation is attached and further proliferate.

14. The method of claim 13, wherein the substrate is collagen.

15. The method of claim 13, wherein the preparation is in the form of a sheet.

16. The method of claim 13, wherein the transplanting comprises performing a corneoscleral incision.

17. The method of claim 16, wherein the transplanting further comprises removing corneal endothelial cells from the eye of the patient following the corneoscleral incision.

18. The method of claim 17, wherein the transplanting further comprises washing the anterior chamber of the eye of the patient with an intraocular perfusion fluid.

19. The method of claim 18, wherein the transplanting further comprises injecting sodium hyaluronate to maintain the space in the anterior chamber.

20. The method of claim 19, wherein the corneal endothelial preparation is inserted into the anterior chamber.

21. The method of claim 20, wherein the transplanting further comprises injecting air into the anterior chamber.

22. The method of claim 21, wherein the transplanting further comprises maintaining the patient face up.

23. The method of claim 22, wherein the transplanting further comprises suturing the sclerocorneal wound.

24. A method of proliferating a corneal endothelial cell, which comprises a step of transplanting a corneal endothelial preparation capable of cell proliferation in vivo to an eye of a human patient,
wherein the preparation comprises (a) a substrate selected from the group consisting of collagen, gelatin, cellulose, polystyrene, polyester, polycarbonate, poly(N-isopropylacrylamide), polylactic acid, polyglycolic acid, hydroxyapatite, and amniotic membrane, and (b) a cultured corneal endothelial cell layer, wherein the preparation covers 10-50% of the area of a disordered corneal endothelium of the human patient, and wherein the preparation remains attached to the Descemet's membrane or corneal stroma of the patient for at least for 3 days after transplantation, and thereafter
(1) detaches itself or
(2) loses the substrate, and
wherein the transplanted corneal endothelial cells grow on the corneal stroma or Descemet's membrane in the vicinity of the site where the preparation is attached and further proliferate.

25. The method of claim 24, wherein the substrate is collagen.

26. The method of claim 24, which the preparation is in the form of a sheet.

27. The method of claim 24, wherein the transplanting comprises performing a corneoscleral incision.

28. The method of claim 27, wherein the transplanting further comprises removing corneal endothelial cells from the eye of the patient following the corneoscleral incision.

29. The method of claim 28, wherein the transplanting further comprises washing the anterior chamber of the eye of the patient with an intraocular perfusion fluid.

30. The method of claim 29, wherein the transplanting further comprises injecting sodium hyaluronate to maintain the space in the anterior chamber.

31. The method of claim 30, wherein the corneal endothelial preparation is inserted into the anterior chamber.

32. The method of claim 31, wherein the transplanting further comprises injecting air into the anterior chamber.

33. The method of claim 32, wherein the transplanting further comprises maintaining the patient face up.

34. The method of claim 33, wherein the transplanting further comprises suturing the sclerocorneal wound.

35. A method of treating a disease selected from the group consisting of bullous keratopathy, corneal edema, corneal leukoma and corneal endothelial inflammation, which comprises transplanting a corneal endothelial preparation capable of cell proliferation in vivo, to an eye of a human subject in need thereof,
wherein the preparation comprises (a) a substrate selected from the group consisting of collagen, gelatin, cellulose, polystyrene, polyester, polycarbonate, poly(N-isopropylacrylamide), polylactic acid, polyglycolic acid, hydroxyapatite, and amniotic membrane, and (b) a cultured corneal endothelial cell layer, wherein the preparation covers 10-50% of the area of a disordered corneal endothelium of the subject,
wherein the preparation is in the form of a sheet,
wherein the preparation is attached to the Descemet's membrane or corneal stroma of the subject for at least 3 days after transplanting the corneal endothelial preparation, and thereafter
(1) detaches itself or
(2) loses the substrate, and
wherein the transplanted corneal endothelial cells grow on the corneal stroma or Descemet's membrane in the vicinity of the site where the preparation is attached and further proliferate, thereby treating the disease.

36. The method of claim 35, wherein the preparation is attached to the Descemet's membrane or corneal stroma of the subject for at least 3 days after transplanting the corneal endothelial preparation, and thereafter (1) detaches itself.

37. The method of claim 35, wherein the preparation is attached to the Descemet's membrane or corneal stroma of the subject for at least 3 days after transplanting the corneal endothelial preparation, and thereafter (2) loses the substrate.

38. The method of claim 35, wherein the transplanting comprises performing a corneoscleral incision.

39. The method of claim 38, wherein the transplanting further comprises removing corneal endothelial cells from the eye of the subject following the corneoscleral incision.

40. The method of claim 39, wherein the transplanting further comprises washing the anterior chamber of the eye of the subject with an intraocular perfusion fluid.

41. The method of claim 40, wherein the transplanting further comprises injecting sodium hyaluronate to maintain the space in the anterior chamber.

42. The method of claim 41, wherein the corneal endothelial preparation is inserted into the anterior chamber.

43. The method of claim 42, wherein the transplanting further comprises injecting air into the anterior chamber.

44. The method of claim 43, wherein the transplanting further comprises maintaining the subject face up.

45. The method of claim 44, wherein the transplanting further comprises suturing the sclerocorneal wound.

\* \* \* \* \*